United States Patent
Russell

(10) Patent No.: US 7,108,762 B2
(45) Date of Patent: Sep. 19, 2006

(54) METHOD FOR MANUFACTURING AN ORIFICE MECHANISM CAPABLE OF LOW FLUID FLOW RATES

(75) Inventor: Scott M. Russell, San Jose, CA (US)

(73) Assignee: Cordis Corporation, Miami Lakes, FL (US)

( * ) Notice: Subject to any disclaimer, the term of this patent is extended or adjusted under 35 U.S.C. 154(b) by 338 days.

(21) Appl. No.: 10/460,554

(22) Filed: Jun. 12, 2003

(65) Prior Publication Data

US 2004/0254563 A1 Dec. 16, 2004

(51) Int. Cl.
B65H 81/00 (2006.01)
A61K 9/22 (2006.01)
A61F 13/00 (2006.01)

(52) U.S. Cl. .............. 156/172; 604/891.1; 424/422
(58) Field of Classification Search ............... 156/172
See application file for complete search history.

(56) References Cited

U.S. PATENT DOCUMENTS

| | | | |
|---|---|---|---|
| 2,146,823 A * | 2/1939 | Karmazin ............... 138/42 |
| 2,323,115 A | 6/1943 | Bryant |
| 2,532,019 A | 11/1950 | Goldberg |
| 3,951,147 A | 4/1976 | Tucker et al. |
| 3,998,244 A | 12/1976 | Bentley |
| 4,176,683 A | 12/1979 | Leibinsohn |
| 4,411,292 A | 10/1983 | Schiller |
| 4,455,144 A | 6/1984 | Michaels |
| 4,564,364 A | 1/1986 | Zaffaroni et al. |
| 4,634,434 A | 1/1987 | Marino, Jr. et al. |
| 4,969,884 A | 11/1990 | Yum |
| 5,122,128 A | 6/1992 | Cardinal et al. |
| 5,267,979 A | 12/1993 | Appling et al. |
| 5,318,558 A | 6/1994 | Linkwitz et al. |
| 5,495,963 A | 3/1996 | Miller et al. |
| 5,554,114 A | 9/1996 | Wallace et al. |
| 5,819,775 A | 10/1998 | Holloway |
| 5,855,713 A | 1/1999 | Harvey |
| 5,985,305 A | 11/1999 | Peery et al. |
| 6,053,903 A | 4/2000 | Samson |
| 6,156,331 A | 12/2000 | Peery et al. |
| 6,261,584 B1 | 7/2001 | Peery et al. |
| 6,270,483 B1 | 8/2001 | Yamada et al. |
| 6,508,804 B1 | 1/2003 | Sarge et al. |
| 6,524,302 B1 | 2/2003 | Kelley |
| 6,524,305 B1 | 2/2003 | Peterson et al. |
| 2003/0088236 A1 | 5/2003 | Johnson et al. |
| 2004/0254565 A1 | 12/2004 | Russell |
| 2004/0267241 A1 | 12/2004 | Russell |

FOREIGN PATENT DOCUMENTS

| | | |
|---|---|---|
| CH | 435 557 A | 5/1967 |
| DE | 199 34 445 A1 | 2/2001 |

(Continued)

OTHER PUBLICATIONS

European Search Report EP 04 25 3356 dated Oct. 4, 2004.

(Continued)

Primary Examiner—Jeff H. Aftergut
(74) Attorney, Agent, or Firm—Louis J. Capezzuto

(57) ABSTRACT

A method for manufacturing an orifice mechanism includes the steps of providing a mandrel having a length and helically wrapping a winding around at least a portion of the length of the mandrel. The mandrel and the winding define a first channel for carrying a drug therethrough. An inlet is at one end of the winding and an outlet is at the other end of the winding.

22 Claims, 7 Drawing Sheets

FOREIGN PATENT DOCUMENTS

| | | |
|---|---|---|
| EP | 0 521 968 B1 | 10/1993 |
| EP | 0 935 976 B1 | 12/2003 |
| WO | WO 94/07562 A1 | 4/1994 |
| WO | WO 98/42317 A2 | 10/1998 |
| WO | WO 02/07810 A2 | 1/2002 |
| WO | WO 03/045352 A2 | 6/2003 |

OTHER PUBLICATIONS

European Search Report EP 04 25 3359 dated Oct. 1, 2004.

* cited by examiner

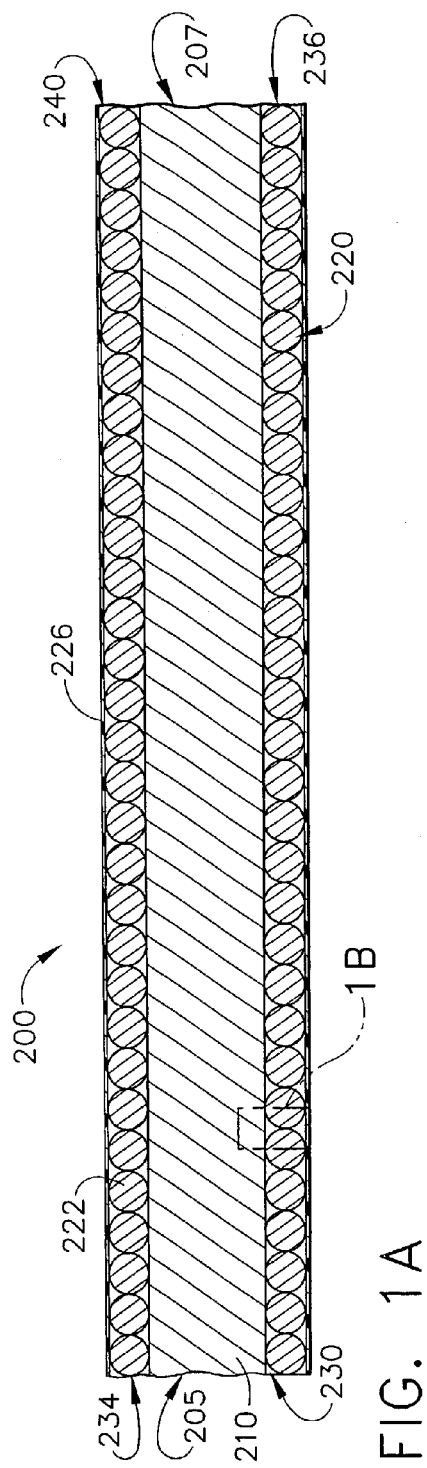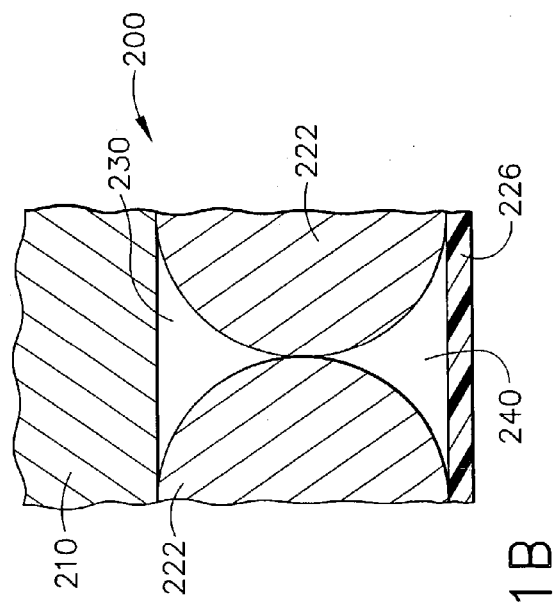
FIG. 1A
FIG. 1B

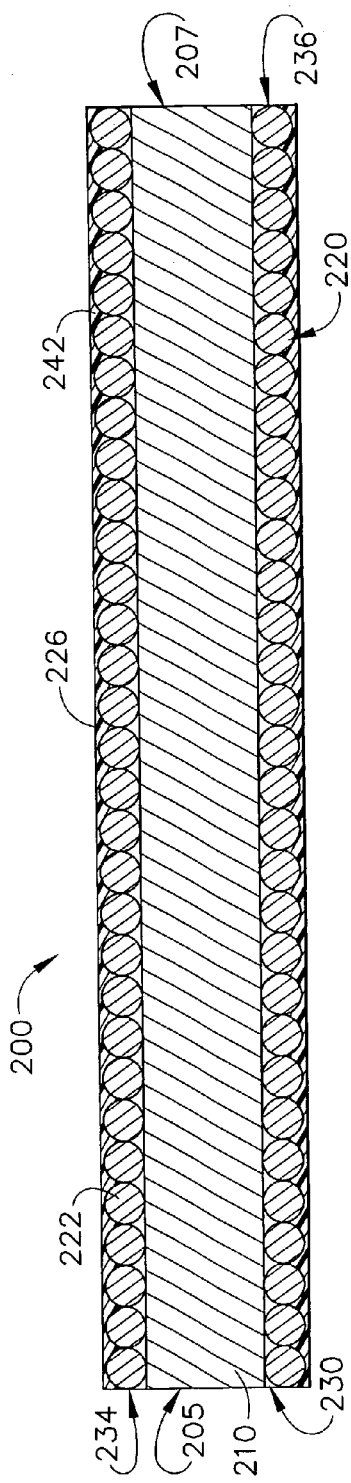
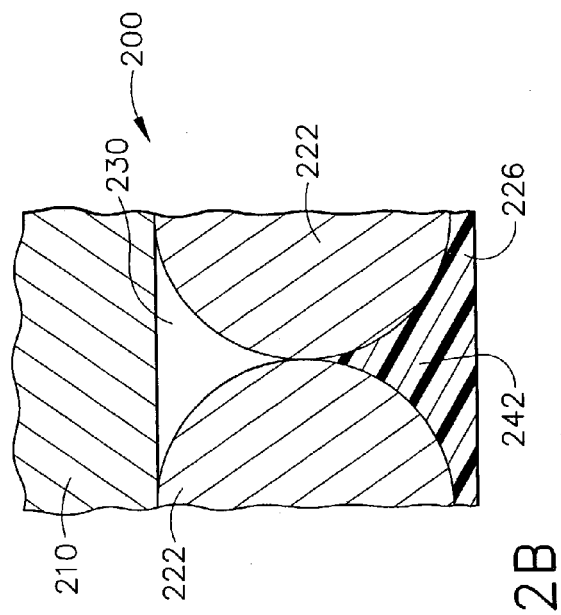
FIG. 2A
FIG. 2B

METHOD FOR MANUFACTURING AN ORIFICE MECHANISM CAPABLE OF LOW FLUID FLOW RATES

FIELD AND BACKGROUND OF THE INVENTION

The present invention relates, in general, to drug delivery, and in particular, to a new and useful device for delivering drugs to the body of a patient at a very low fluid flow rate. The present invention also includes the method of manufacture of the novel drug delivery device.

Fluid delivery devices, and particularly, drug delivery devices are known. Additionally, it is also known within the fluid delivery or drug delivery field, that fluids, such as drugs, can be moved through helical flow paths. For example, U.S. Pat. No. 3,998,244 (Bentley) describes a drip irrigation valve with a helical flow path for the delivery of various agricultural liquids, such as fertilizers to be fed through an irrigation system. This particular system is useful for providing drip irrigation that conserves water, minimizes weed growth and facilitates the transport of the agricultural liquids through the irrigation system.

U.S. Pat. No. 4,176,683 (Leibinsohn) describes a flow regulator useful in apparatus designed for administering liquids to the body. The device is a presettable fluid flow regulator having an elongated sleeve of flexible material and a core within the sleeve having a helical recess of varying cross section carved or scored into the core. A ring on the outside of the sleeve has an internal diameter slightly less than the outer diameter of the sleeve and is used to squeeze the sleeve against the core to define a flow passage between the core and the sleeve. The volume of flow is determined by the longitudinal position of the ring along the sleeve.

U.S. Pat. No. 6,270,483 (Yamada et al.) describes a liquid discharge regulator and a liquid feeder that utilizes a liquid discharge regulator. The regulator has a channel spirally carved or formed on the surface of a passage forming member. The surface of the passage forming member is brought into close contact with the inner surface of a housing part wherein the channel functions as a liquid passage. The passage forming member is made of a plastic material by using injection molding manufacturing and mass production. The main purpose behind using the plastic material made exclusively through the injection molding process for the formation of the passage forming member is aimed at reducing manufacturing costs of the regulator.

U.S. Pat. No. 5,985,305 (Peery et al.) describes a back-diffusion regulating outlet consisting of a male threaded member in threaded relationship with a smooth interior surface of a reservoir thereby forming a helical flow path. As clearly shown, similar to the other prior art flow regulator devices, the regulating outlet consists of a solid core of material which serves as a male threaded member, i.e. a screw, that is in mating relationship with the smooth interior surface of the reservoir.

To date, there have been no fluid flow regulator devices, mechanisms or drug delivery devices using these type of mechanisms that can be provided or manufactured in an extremely efficient manner, easily and readily adaptable to any desired designed configuration, and having extremely low cost of manufacturing.

SUMMARY OF THE INVENTION

The present invention is directed toward the field of drug delivery and relates to a novel orifice feature, mechanism or drug regulator device such as an orifice device. The present invention also relates to a drug delivery device utilizing the novel orifice mechanism and includes a novel implantable pump, a novel drug delivery device such as a drug delivery catheter or a novel implantable drug delivery device such as an implantable drug pump.

For purposes of this disclosure, the term "drug" means any type of molecules or compounds deliverable to a patient to include being deliverable as a fluid, slurry or fluid-like manner. The term "drug" is also defined as meaning any type of therapeutic agent or diagnostic agent which can include any type of medicament, pharmaceutical, chemical compounds, dyes, biological molecules to include tissue, cells, proteins, peptides, hormones, signaling molecules or nucleic acids such as DNA and RNA.

One embodiment of the present invention is an orifice device such as an orifice mechanism or drug dispenser regulator or regulator feature (all commonly referred to herein as "orifice device" or "orifice mechanism" or "orifice"). In accordance with the present invention, the orifice device is used to deliver a drug and comprises an inner member having a proximal end and a distal end and a winding helically wound around the inner member. The winding and the inner member define a first channel for carrying a drug therethrough (an active channel). An inlet is at the proximal end of the winding and an outlet is at the distal end of the winding.

Another embodiment of the present invention is a device for delivering a drug wherein the device comprises a body having a proximal end and a distal end and an opening in the distal end of the body. An orifice mechanism is included at the distal end of the body and is in fluid communication with the opening. The orifice mechanism comprises an inner member having a proximal end and a distal end and a winding helically wound around the inner member. The winding and the inner member define a first channel for carrying a drug therethrough (an active channel) and an inlet at the proximal end of the winding and an outlet at the proximal end of the winding.

In this embodiment according to the present invention, the novel device is a drug delivery device such as a drug delivery catheter or an infusion port device such as an intravenous (IV) port or IV fluid or drug delivery device.

Another embodiment of the present invention is a novel implantable device for delivering a drug wherein the device comprises a housing and a source of drug contained within the housing. An orifice mechanism is located at, on or within the housing and fluidly communicates with the source of drug. The orifice mechanism comprises an inner member having a proximal end and a distal end and a winding helically wound around the inner member. The winding and the inner member define a first channel for carrying the drug therethrough (an active channel) and an inlet at the proximal end of the winding and an outlet at the distal end of the winding. The drug is carried by the orifice mechanism and dispensed outside of the housing. The novel implantable device according to the present invention is designed as either a temporary or a permanent device to be implanted in a patient's body, particularly, at any location on or within the patient's body such as a particular site within tissue or organs.

Another embodiment of the present invention is a novel method for manufacturing an orifice mechanism. The novel method in accordance with the present invention comprises the steps of providing a mandrel, i.e. any member which serves as an inner member or core, wherein the mandrel has a certain length. A winding is then helically wound around at least a portion of the length of the mandrel. The mandrel and the winding define a first channel for carrying a drug therethrough (an active channel). An inlet is at one end of the winding and an outlet is at another end of the winding for ingress and egress of the drug respectively.

All embodiments of the present invention are directed toward a simple orifice design that allows for exceptionally low fluid flow rates by creating an extremely long orifice with a very small cross-sectional area that is ideal for very compact spaces. The use of a helical winding for all embodiments of the present invention results in a simple helical wire wrap that creates a very long orifice and results in primary benefits such as simplicity, compactness, readily adaptable design and customizable designs, ease of manufacturing and low costs of parts for manufacturing. The flexibility and adaptability of the present invention is exhibited by the properties of the orifice in accordance with the present invention that can be easily modified, for instance, by selecting a winding (comprised of any desired wire type) using wires of different diameters and also by varying the length of the helix (helical winding). Assembly and manufacturing of the orifice in accordance with the present invention is extremely flexible and simple especially since no precision machining is required such as the precise machining or complex and expensive injection molding equipment associated with the prior art devices and their manufacturing methods.

BRIEF DESCRIPTION OF THE DRAWINGS

FIG. 1A is an elevated side view of an orifice device in cross-section having a two-channel design in accordance with the present invention;

FIG. 1B is an enlarged view of a portion of the orifice device of FIG. 1A showing a coil as part of a winding and having a circular-shaped cross-section;

FIG. 2A is an elevated side view of an alternative embodiment of an orifice device in cross section having a one-channel design in accordance with the present invention;

FIG. 2B is an enlarged view of a portion of the orifice device of FIG. 2A showing a coil as part of a winding and having a circular-shaped cross-section;

DESCRIPTION OF THE PREFERRED EMBODIMENTS

The present invention is directed toward a novel orifice mechanism, generally designated 200, (interchangeably and commonly referred to herein as "orifice mechanism", "orifice feature", "orifice", "regulator", "regulator mechanism", "regulator device", or "orifice device") such as reflected in embodiments of the present invention shown in FIGS. 1A, 1B, 2A, 2B, FIG. 3, FIG. 4, FIG. 5, FIG. 6, FIG. 7.

Figure 8:
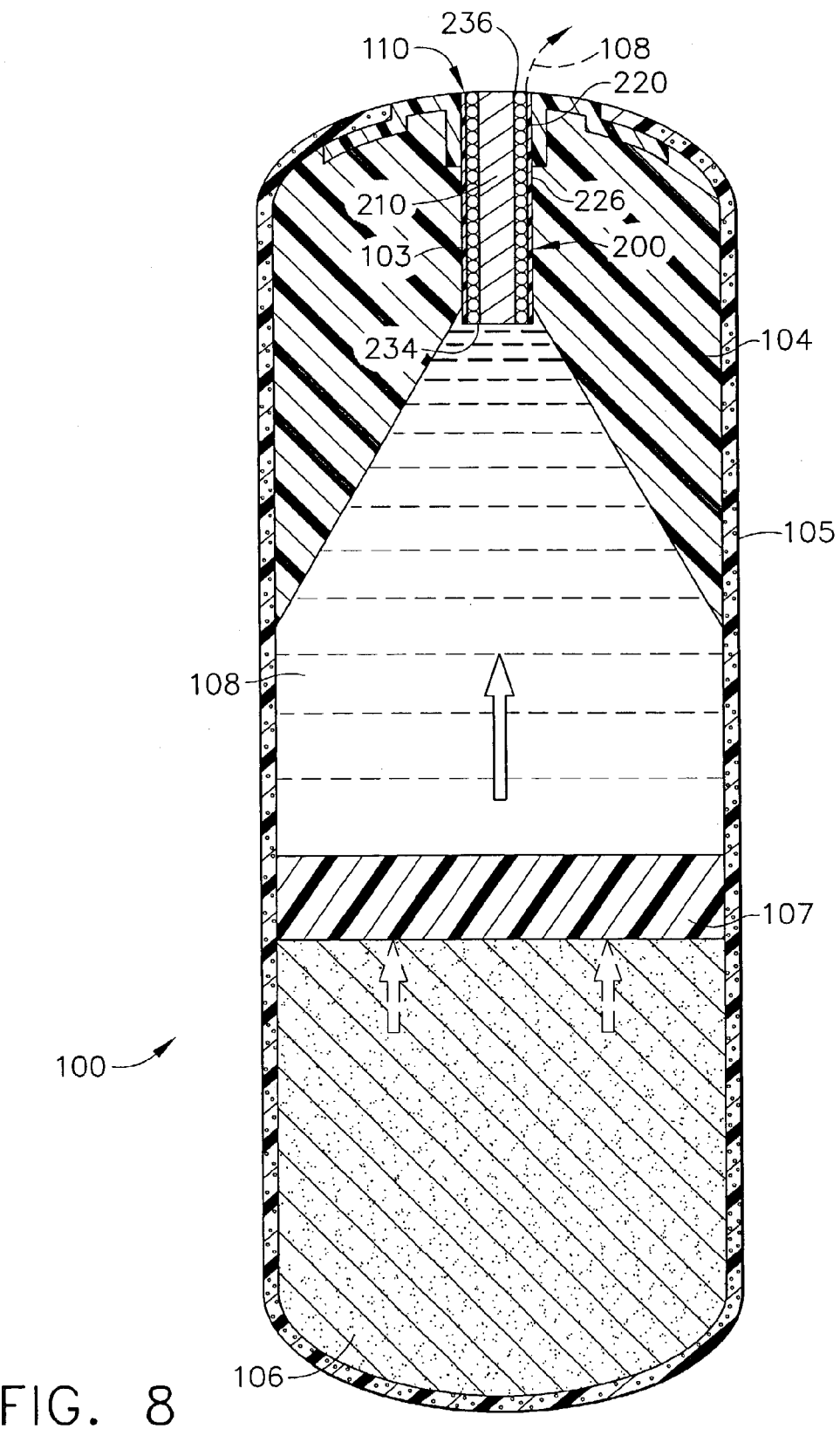
FIG. 8 is a view in cross-section of an implantable drug delivery device having an orifice mechanism in accordance with the present invention.

The present invention is also directed toward a novel drug delivery device such as an implantable device, generally designated 100, shown in FIG. 8 and includes any type of implantable device such as an implantable drug delivery device, implantable drug elusion device, implantable drug delivery pumps or the like. The novel drug delivery device 100 of this embodiment also includes the novel orifice mechanism 200.

Figure 9:
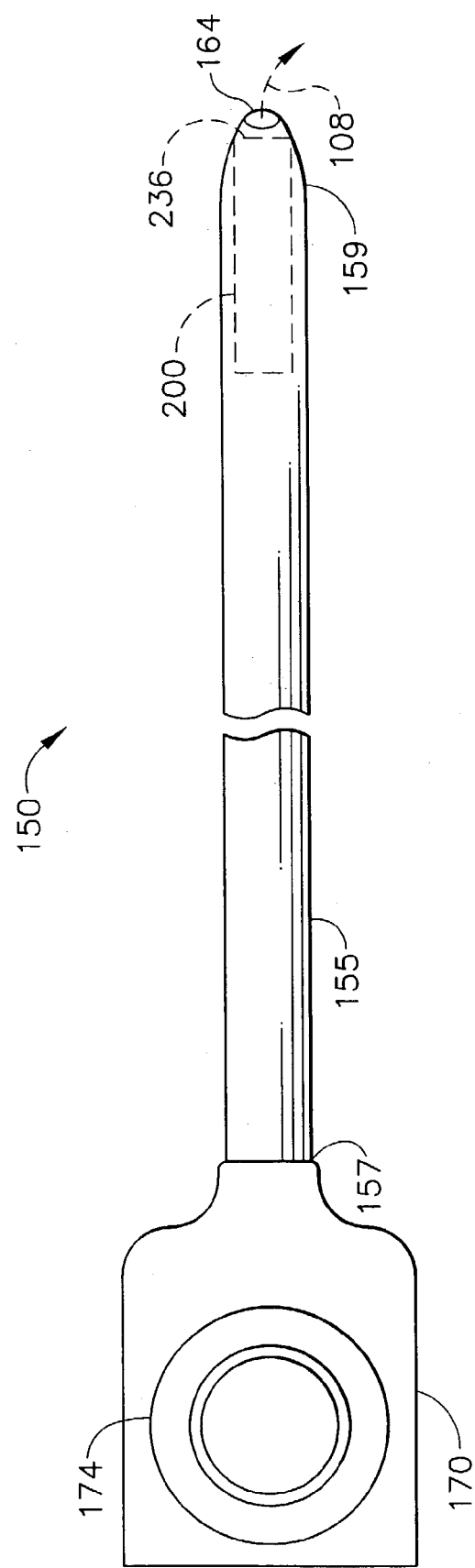
FIG. 9 is a side view of an elongated drug delivery device having an orifice mechanism in accordance with the present invention.

The present invention is also directed toward a novel drug delivery device 150 having an elongated body 155 utilizing the orifice mechanism 200 in accordance with the present invention which is used at a desired location on the body 155 of the drug delivery device 150 such as shown in FIG. 9. The drug delivery device 150 in accordance with the present invention in this embodiment shown in FIG. 9 is directed toward drug delivery devices such as drug delivery catheters having elongated and/or flexible bodies and also include intravenous (IV) drug catheters such as IV drug catheters or IV drug delivery ports or local drug delivery catheters.

The present invention is also directed toward a novel method of manufacturing the orifice mechanism 200 in accordance with the present invention and as best illustrated in FIG. 1A and FIG. 2A.

As best shown in FIGS. 1A, 1B, 2A and 2B, the novel orifice device or mechanism 200 in accordance with the present invention has a first end or proximal end 205 and a second end or distal end 207 respectively. The first component of the orifice mechanism 200 in accordance with the present invention is an inner member 210 which serves as an inner core for the device 200 and is used as a mandrel in the manufacturing method in accordance with the present invention. The inner member 210 has a length of any desired dimension and a winding 220 comprising a wire strand (wire) 222 helically wound or helically wrapped around the inner member (mandrel) 210 along any desired portion of the inner member 210. For example, the wire 222 of the winding 220 extends from the proximal end 205 to the distal end 207 of the orifice mechanism 200 as illustrated in FIGS. 1A and 2A, however, the winding 220 can be located along any portion of the length of the inner member 210 and comprises any desired width or dimension along the length of the inner member 210.

The wire 222 of the winding 220 is wound or wrapped around the inner member 210 in any desired or customized fashion in order to create any desired pitch (channel depth) and amplitude (distance between adjacent individual strands of wire 222) in order to customize a first drug delivery channel or inner drug delivery channel 230. This first drug delivery channel is also known as an active channel. The first drug delivery channel 230 is an interior channel formed by the individual strands of the wire 222 of the winding 220 and an outer member 226 which is an exterior surface placed over and around the winding 220 and inner member 210. The outer member 226 serves as an exterior surface which constrains the winding 220 (and individual strands of wire 222) and the inner member 210 such that the outer member 226, the wire 222 of the winding 220, and the inner member 210 (mandrel) define a second drug delivery channel or exterior channel formed by the remaining or unfilled interstices or interstitial spaces. The second drug delivery channel is also an active channel. The outer member 226 can be any type of member such as a sleeve or a tube as relevant examples, and can be made of any material such as a polymer material, for instance, PTFE, or even be made entirely of an adhesive material such as a glue.

Figure 3:
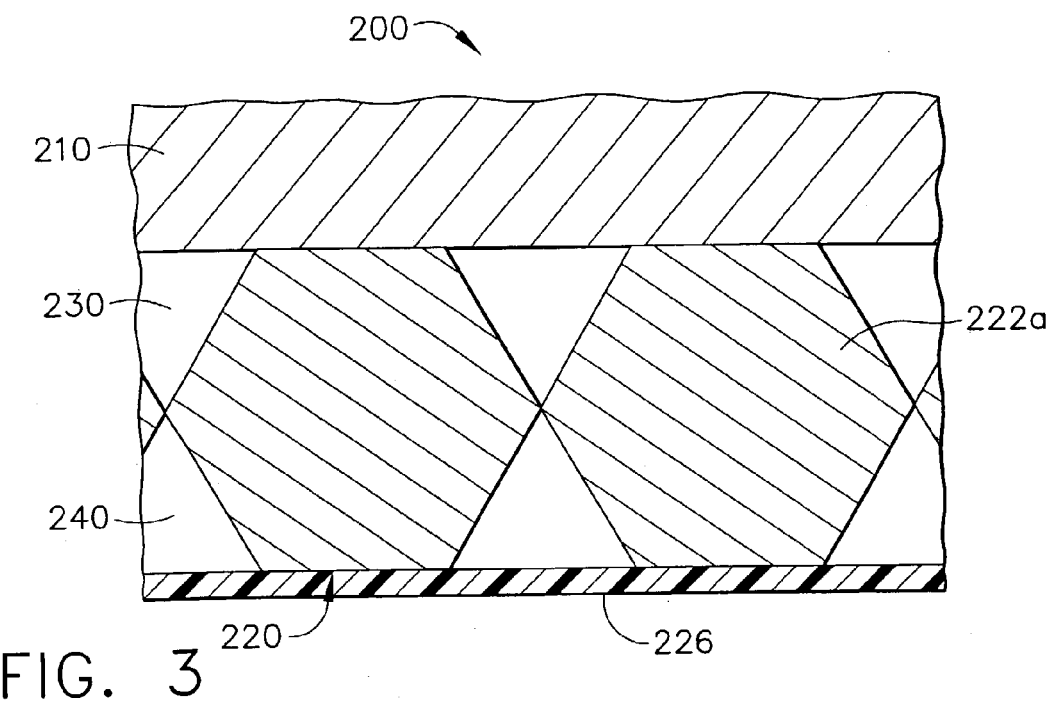
FIG. 3 is an enlarged view of a portion of the orifice device of FIG. 1A wherein the coil has a hexagonal shape in cross-section.
Figure 4:
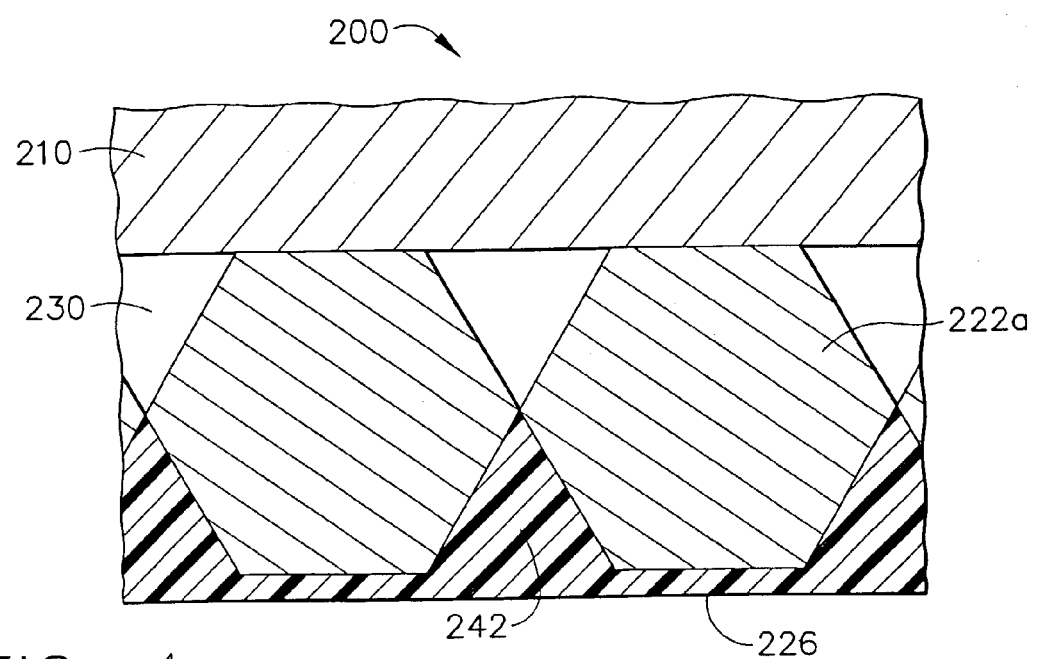
FIG. 4 is an enlarged view of a portion of the orifice device of FIG. 2A wherein the coil has a hexagonal shape in cross-section.
Figure 5:
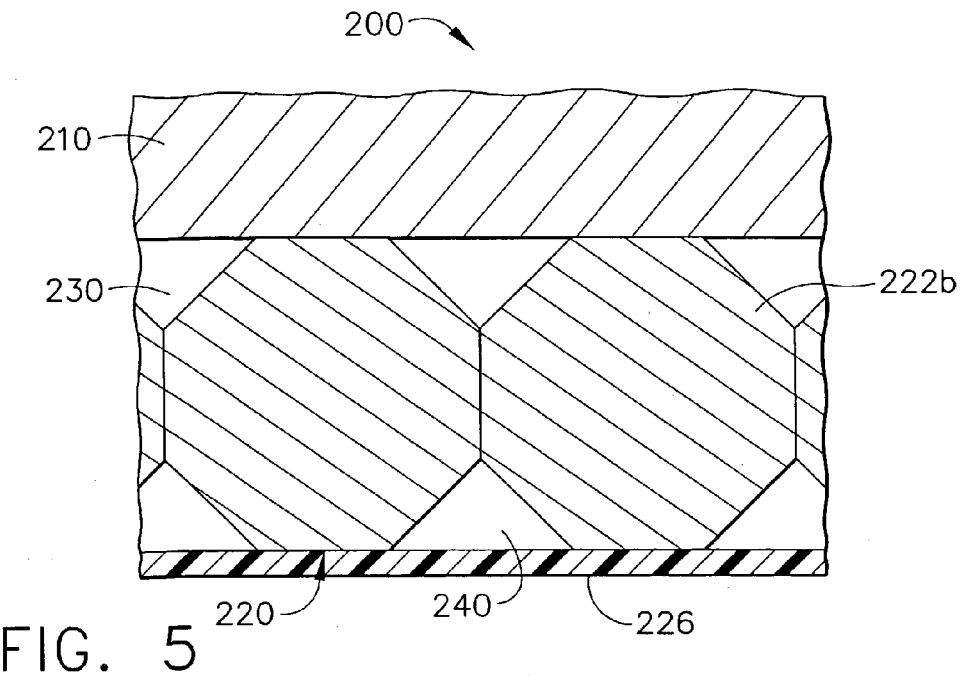
FIG. 5 is an enlarged view of a portion of the orifice device of FIG. 1A wherein the coil has an octagonal shape in cross-section.
Figure 6:
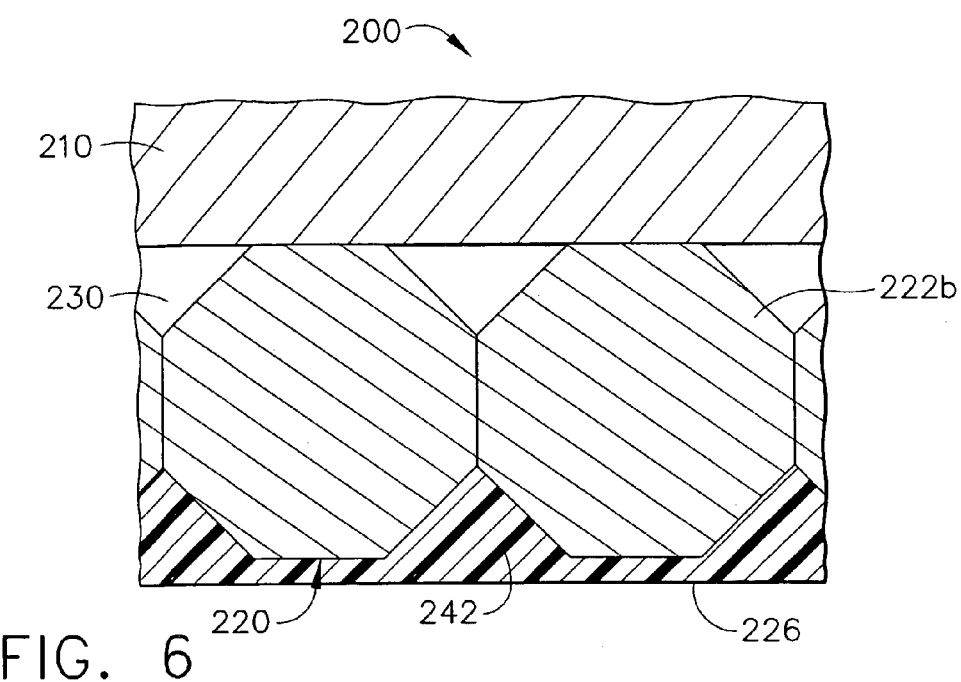
FIG. 6 is an enlarged view of a potion of the orifice device of FIG. 2A wherein the coil has an octagonal shape in cross-section.
Figure 7:
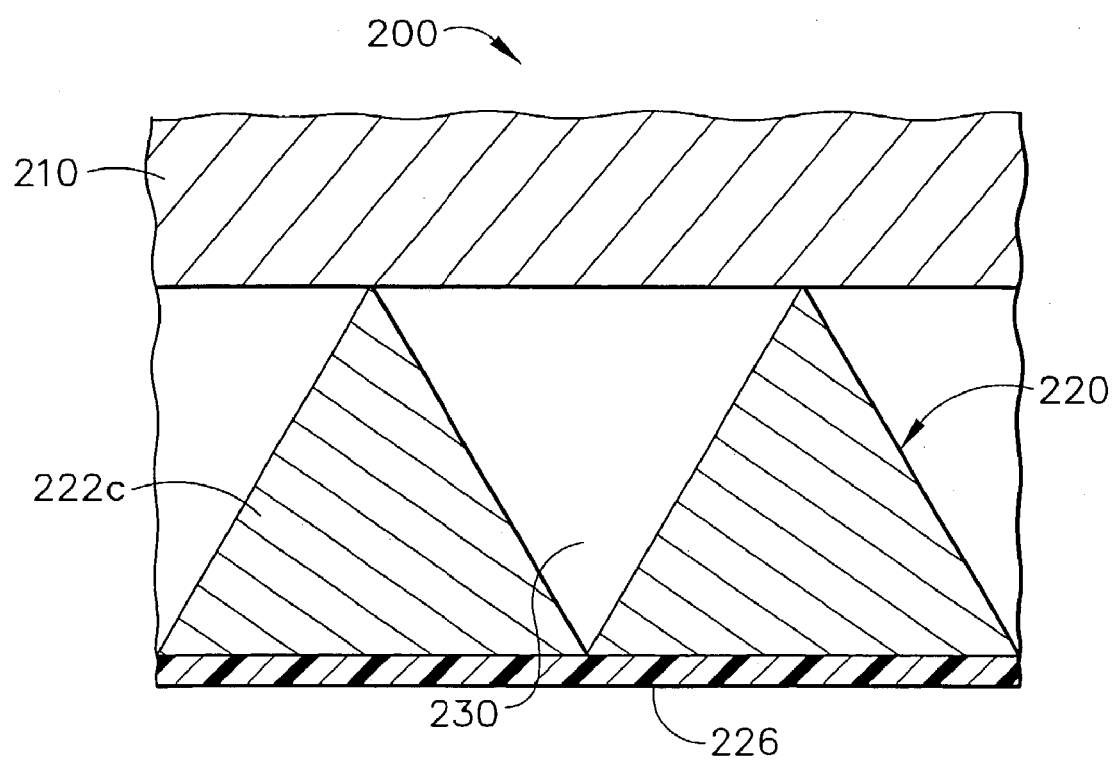
FIG. 7 is an enlarged view of a portion of the orifice device of FIG. 2A wherein the coil has a triangular shape in cross-section.

The wire 222 is made of a degradation resistant material in order to resist erosion or degradation by the constituents or properties of the drug or by exerted forces applied by the drug 108 (FIG. 8) when delivered or channeled through the interior channel 230 (FIGS. 1A, 1B, 2A and 2B) and the exterior channel 240 (FIGS. 1A and 1B). Examples of degradation resistant materials for use with the wire 222 in accordance with the present invention include materials such as a nickel titanium alloy, i.e. Nitinol (NiTi), stainless steel alloys, plastic or other types of relevant polymers. As best illustrated in FIGS. 1B, 2B, 3, 4, 5, 6 and 7, the wire 222 comprises any desired cross-sectional shape or configuration. Although not limited to these particular depicted cross-sectional shapes or configurations, relevant examples of the wire 222 in accordance with the present invention include wire 222 having a circular-shaped cross-sectional configuration as shown in FIG. 1B and FIG. 2B; wire 222a having a hexagonal shape in cross-section as shown in FIG. 3 and FIG. 4; octagonal-shape wire 222b as shown in FIG. 5 and FIG. 6; and triangular-shape wire 222c in cross-section as shown in FIG. 7.

When manufacturing the orifice mechanism 200 in accordance with the present invention, the interior channel (the inside or interior set of interstices) 230 or exterior channel (the exterior or outside set of interstices) 240 can be blocked in order to created a one-channel or one-side design or approach in order to further reduce the flow of the drug 108 (FIG. 8) or to ease the burden of manufacturing. For example, this can be accomplished without precise sizing of the outer member 226, and instead can be accomplished through the use of a polymer material or glue as the outer member 226 in lieu of an outer member 226 as a sleeve or tube. Thus, in a one-channel design, channel filling material 242 (FIG. 2B, FIG. 4, and FIG. 6) is used to occlude or block one of either the interior channel (interior interstices) 230 or exterior channel (exterior interstices) 240 as shown. For example, in the embodiments shown, it is the exterior channel (exterior interstices) 240 that is replaced by the channel filling material 242, i.e. the polymer material or glue. Although not shown, alternatively, the channel filling material 242 is used to occlude, block or fill the interior channel (interior interstices) 230 as part of a one-channel design. Additionally, the channel filling material 242 can be either the same material as used with the outer member 226 or be made of a second different material.

Accordingly, in accordance with the manufacturing method of the present invention, the orifice device or orifice mechanism 200 is adaptable to a tailored or customizable manufacturing method determined by control factors in accordance with the present invention. Thus, the present invention allows for customizing these central factors upon demand and include overall length of the winding 220, cross-sectional area of the wire 222 (to include the alternative wire embodiments 222a, 222b and 222c), shapes or configurations of all wire configurations, and dimensions of the interstices or channels, i.e. interior channel 230 and/or exterior channel 240; and the amount of constrain or fit of outer member 226 to include the dimensions, shape and specific material of the outer member 226. Thus, all of these factors controlled by the manufacturing method in accordance with the present invention allows for a customized orifice or orifice mechanism 200 that allows for varying rates of fluid flow control or regulation for the drug 108 (FIG. 8).

As a drug delivery feature, the orifice device or orifice mechanism 200 includes an inlet 234 located at the first strand of wire 222 at the inner member 210, for example, located at the proximal end 205 of the orifice mechanism 200. The inlet 234 is the starting point or entry point for ingress of the drug 108 (FIG. 8) into the first channel or interior channel 230 for carrying and channeling therethrough and terminates in an outlet 236 at the last strand of wire 222 of the winding 220 at the opposite end of the winding 220, for example, at the distal end 207 of the orifice mechanism 200. The outlet 236 allows for the channeled drug 108 (FIG. 8) to exit or egress from the last strand of wire 222 of the winding 220, for example, at distal end 207. As shown in FIG. 1A, the inlet 234 and the outlet 236 will exist at the interior channel or first channel 230 and the second channel or exterior channel 240 respectively as shown such that both channels 230 and 240 are active channels. As shown in FIG. 2A, the inlet 234 and the outlet 236 will exist for the first channel or interior channel 230 only. Thus, the channel filling material 242 of the outer member 226 prevents ingress, channeling and egress of any drug 108 through any other portion of the orifice device 200 except for the first channel or inner channel 230, for example, channeling is only possible through the interior interstices defined by the interior channel 230. Accordingly, in this example, inner channel 230 is the only active channel capable of channeling the drug 108 through its interstices.

Relevant examples of degradation resistant material for the winding 220, i.e. wire 222 (FIG. 1A, FIG. 1B, FIG. 2A and FIG. 2B), wire 222a (FIG. 3 and FIG. 4), 222b (FIG. 5 and FIG. 6), and 222c (FIG. 7), also include various types of metal such as stainless steel alloys, nickel titanium alloys (Nitinol, NiTi), MP35N, and Titanium as well as various types of polymers or plastics.

Moreover, any size or dimensions for the winding 220 and wire 222, 222a, 222b and 222c respectively can be utilized. For instance, one example of appropriate dimensions for the wire is to use wire having a strand with a width ranging from 0.001–0.050 inches. Additionally, another preferable example for the wire dimensions in accordance with the present invention, is to utilize a wire having strands with a width ranging from 0.004–0.005 inches.

The present invention also is directed toward an implantable drug delivery device, generally designated 100, which includes implantable devices such as a drug delivery pump. In one example according to the present invention, the drug delivery device 100 is an implantable drug pump which utilizes the orifice mechanism 200 and a source of drug 108.

FIG. 8, shows orifice mechanism 200 in an implantable pump device 100 such as an osmotically driven ruminal bolus. The orifice 200 resides in space 103 which passes through a densifier 104. The bolus is surrounded by a semipermeable membrane 105. The semipermeable membrane 105 allows water to pass therethrough which is imbibed by swellable osmotic element 106 which abuts or contacts movable interface 107 and upon imbibing, the water exerts force upon moveable interface 107 which in turn forces the drug 108 out of the orifice 200 through the outlet 236.

The semipermeable mebrane 105 serves as a housing. Additionally, the membrane or housing 105 has an opening 110 therein and in fluid communication with the outlet 236 of the orifice mechanism 200. This permits the drug 108 to be carried by and channeled out of the orifice mechanism 200 and the membrane or housing 105 respectively in order to provide systemic or localized drug delivery.

The present invention is also intended to be not only an implantable drug device, but also intended to be used as a temporary implant device, for example a device wherein all of the components of the device 100, including the orifice mechanism 200, are made of a biocompatible and biodegradable material. Additionally, the drug delivery device 100 is also intended to be used as a device for placement within a body cavity, for example, the nasal cavity, ear canal, mouth, sinus passageway, the eye to include any vitreous passageway, the rectum or the like. Furthermore, the drug delivery device 100 is also intended to be used at an exterior surface of the patient, for example, placed at a location somewhere on the patient's skin for local delivery of the drug 108 to an exterior treatment site on the skins surface or for absorption into the patient's bloodstream through the skin or directly into a wound.

In the drug delivery device embodiment illustrated in FIG. 8, the densifier 104, housing/membrane 105, swellable osmotic element 106 and moveable interface 107 (which can be a piston) operate as a driving system or pumping system for the drug 108 by working in combination to move the drug 108 into inlet 234, through the appropriate interstices or channels (for instance, first channel and/or second channel), and out of the outlet 236 and housing 105 through the opening 110 in housing 105.

FIG. 9 illustrates another embodiment of a drug delivery device, generally designated 150, such as an intravascular device. Relevant examples of the device 150 include a catheter, intravenous (IV) port device or the like. In some instances in accordance with the present invention, the drug delivery device 150 includes a body 155, such as an elongated body, having a proximal end 157 and a distal end 159 respectively and a lumen therein in fluid communication with the proximal end 157 and the distal end 159. A distal end opening 164 is located at the distal end 159 of the body 155. And, the orifice mechanism 200 is located on the body 155, for example within the lumen of body 155 and at the distal end 159 and adjacent to and in fluid communication with the opening 164. The body 155 serves as the outer member 226 (FIGS. 1A–8) and provides similar function and is comprised of similar materials as used with the outer member 226 (detailed above). The outlet 236 of the orifice mechanism 200 is located near the opening 164 and is in fluid communication therewith such that the drug 108 is passed through the orifice mechanism 200 (as described above) and out of the outlet 236 and opening 164 respectively.

Additionally, the delivery device 150 includes a handle 170 located at the proximal end 157 of the body 155. The handle also includes a control 174 for controlling movement of the distal end 159 of the device 150. Relevant movement of the distal end 159 includes deflection of the distal end 159 and opening 164 in various directions, for example, in any desired direction or angle offset from the longitudinal access of the body 155. Although not shown, the device 150 can either include the source of drug 108 at a location within the lumen body of 155 or can receive the source of drug 108 at any desired portion of the device 150, for example, through an entry port in the handle 170 (not shown). Accordingly, an entry or access port in the handle 170 can be shaped to accommodate a standard needle syringe containing the source of drug 108 such that the drug 108 can be injected or infused into the body 155 of the device 150 through the entry or access port for feeding or supplying drug 108 to the orifice mechanism 200 for ultimate delivery through the opening 164 of the device 150. In addition to the design and control factors mentioned above that are responsible for the fluid flow rate of the drug 108, the drug 108 is also channeled or migrates through the orifice mechanism 200 through capillary action which is controlled by many of the parameters and features outlined above to include tightness of the winding 220 (helical coil), diameter or width of the strands of wire (222, 222a, 222b and 222c respectively) and viscosity of the drug 108 being delivered. All of these parameters can be adjusted in order to optimize the fluid flow rate for the drug 108. Additionally, additives can be included with the drug 108 (in solution) in order to control the viscosity of the drug 108 thereby controlling the overall delivery fluid flow rate.

Moreover, as mentioned above, one benefit of the orifice mechanism or orifice device 200 in accordance with the present invention is the ability to achieve very low fluid flow rates through the use of a tight, economic and cost efficient manufactured winding 220. Thus, the present invention allows for more efficient manufacturing, less parts and less manufacturing tooling normally associated with the traditional and more costly parts, tools and manufacturing methods associated with the prior art drug delivery devices. Accordingly, the present invention avoids these drawbacks associated with the prior art devices such as costly machining normally found with lathe machines, micro-drilling or even injection molding machines that are required for manufacturing these prior art devices.

It will be appreciated that the preferred embodiments described above are cited by way of example and the full scope of the invention is limited only by the claims which follow.

What is claimed is:

1. A method of making a drug delivery device having a customized orifice mechanism, the method comprising the steps of:
   providing a mandrel having a length;
   selecting a winding comprising a desired wire type and a desired length;
   helically wrapping the winding around at least a portion of the length of the mandrel; and
   the mandrel and the winding defining a first channel for carrying a drug therethrough and an inlet at one end of the winding and an outlet at another end of the winding.

2. The method according to claim 1, further comprising using a wire for the winding.

3. The method according to claim 2, further comprising providing an outer member over the winding.

4. The method according to claim 3, further comprising using the winding and the outer member to define a second channel for also carrying a drug therethrough.

5. The method according to claim 4, further comprising using an outer member comprising a channel filling material for blocking drug flow through the second channel.

6. The method according to claim 2, further comprising using a wire having a circular shape in cross-section.

7. The method according to claim 4, further comprising using a wire having a circular shape in cross-section.

8. The method according to claim 2, further comprising using a wire having a hexagonal shape in cross-section.

9. The method according to claim 4, further comprising using a wire having a hexagonal shape in cross-section.

10. The method according to claim 2, further comprising using a wire having an octagonal shape in cross-section.

11. The method according to claim 4, further comprising using a wire having an octagonal shape in cross-section.

12. The method according to claim 2, further comprising using a wire having a triangular shape in cross-section.

13. The method according to claim 3, further comprising using a sleeve as an outer member.

14. The method according to claim 3, further comprising using an outer member comprising a polymer material.

15. The method according to claim 14, further comprising using a polymer material comprising PTFE.

16. The method according to claim 5, further comprising using a glue as a channel filling material.

17. The method according to claim 2, further comprising using a wire comprising made of a degradation-resistant material.

18. The method according to claim 17, further comprising using a material is a nickel titanium alloy.

19. The method according to claim 17, further comprising using a material comprising is a stainless steel alloy.

20. The method according to claim 17, further comprising using a material comprising plastic.

21. The method according to claim 2, further comprising using a wire having a width ranging from 0.001–0.050 inches.

22. The method according to claim 21, further comprising using a wire having a width ranging from 0.004–0.005 inches.

* * * * *